Figure 1:
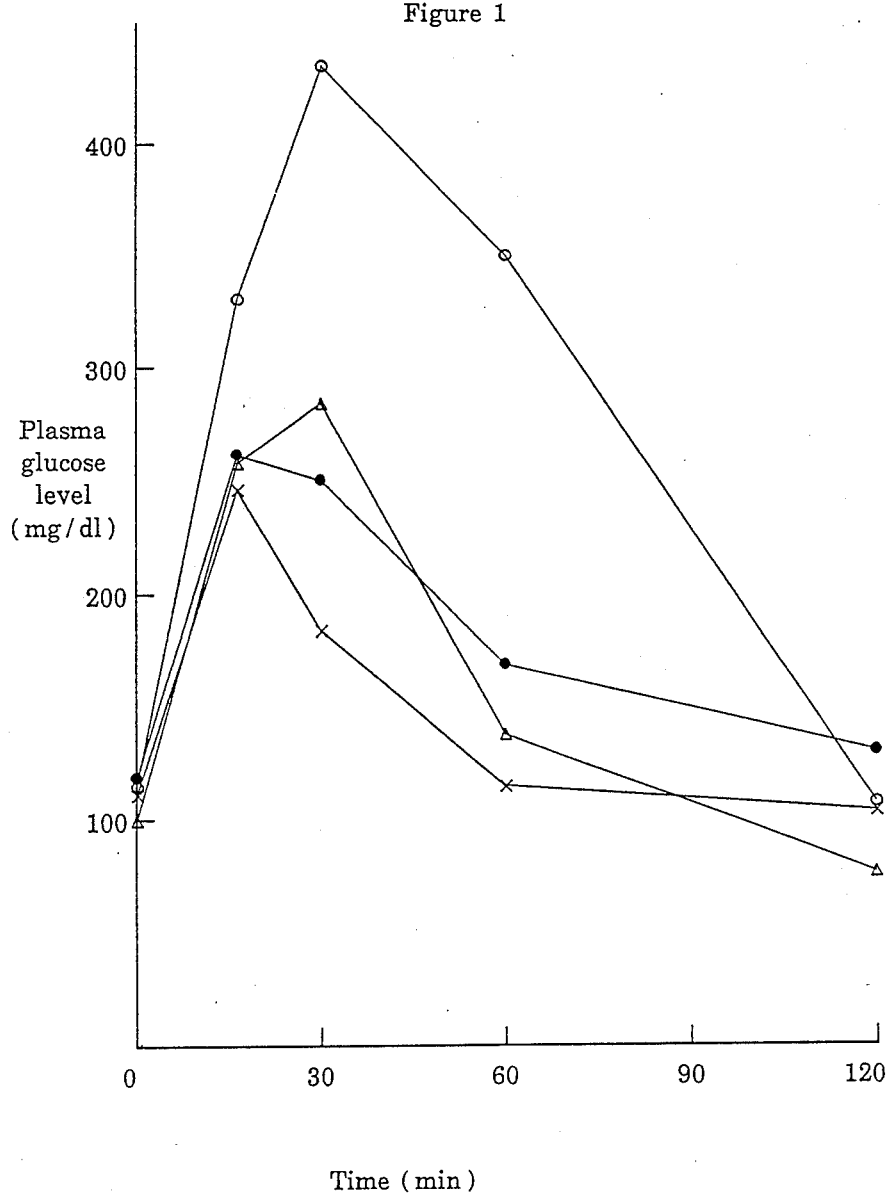

United States Patent [19]

Nakagawa et al.

[11] Patent Number: 4,791,192

[45] Date of Patent: Dec. 13, 1988

[54] CHEMICALLY MODIFIED PROTEIN WITH POLYETHYLENEGLYCOL

[75] Inventors: Yasushi Nakagawa, Kawanishi; Takashi Ito, Osaka, both of Japan

[73] Assignee: Takeda Chemical Industries, Ltd., Osaka, Japan

[21] Appl. No.: 63,400

[22] Filed: Jun. 18, 1987

[30] Foreign Application Priority Data

Jun. 26, 1986 [JP] Japan .................................. 61-151098
Apr. 21, 1987 [JP] Japan .................................. 62-97990

[51] Int. Cl.$^4$ ...................... C07K 15/00; C07K 17/06; A61K 37/36
[52] U.S. Cl. ..................................... 530/399; 424/92; 530/397; 530/406; 530/410; 514/21
[58] Field of Search ............... 530/399, 406, 410, 397; 424/92

[56] References Cited

U.S. PATENT DOCUMENTS

| | | | |
|---|---|---|---|
| 4,179,337 | 12/1979 | Davis et al. ...................... | 530/406 X |
| 4,301,144 | 11/1981 | Iwashita et al. ................. | 530/410 X |
| 4,496,689 | 1/1985 | Mitra ............................... | 530/410 X |
| 4,609,549 | 9/1986 | Nogimori et al. .................. | 424/92 |
| 4,640,835 | 2/1987 | Shimuzu et al. ................. | 435/188 X |
| 4,704,274 | 11/1987 | Sakuma et al. ................... | 424/92 X |

OTHER PUBLICATIONS

J. Biol. Chem. 258, 6758–6761 (1983), Tamura et al.
J. Biol. Chem. 252, 3582–3586 (1977), Abuchowski et al.
Motoyuki Yajima et al., "Islets-Activating Protein (IAP in *Bordetella pertussis* that Potentiates Insulin Secretory Responses of Rate", J. Biochem., vol. 83, pp. 295–303 (1978).
Motoyuki Yajima et al., "Biological Properties of Islets-Activating Protein (IAP) Purified from the Culture Medium of *Bordella pertussis*", J. Biochem., vol. 83, (1978).
Margaret Pittman, "Pertussis Toxin: The Cause of the Harmful and Prolonged Immunity of Whooping Cough. A Hypotesis", Review of Infectious Diseases, vol. 1, pp. 401–412, (1979).
Katsumi Nogimori et al., "Chemical Modification of Islet-Activating Protein, Pertussis Toxin Essential Role of Free Amino Groups in Its Lymphocytosis-Promoting Activity", Biochimia et Biophysica Acta, vol. 801, pp. 220–231 (1984).
Ayako Matsushima et al., "Modification of *E. coli* Asparaginase with 2,4-Bis(O-Methoxypolyethylene Glycol)-6-Chloro-S-Triazine (Activated PEG$_2$); Disappearance of Binding Ability Towards Anti-Serum and Retention of Enzymic Activity", Chemistry Letters, pp. 773–776 (1980).
Japanese Unexamined Patent Laid Open No. 129296/1980.

*Primary Examiner*—Howard E. Schain
*Attorney, Agent, or Firm*—Wegner & Bretschneider

[57] ABSTRACT

The chemically modified protein of the present invention has a strong islet-activating activity and is lower in various side effects than non-modified IAP, so that it may be employed as a prevention and therapeutic drug for diabetes.

16 Claims, 3 Drawing Sheets

CHEMICALLY MODIFIED PROTEIN WITH POLYETHYLENEGLYCOL

The present invention relates to a chemically modified protein.

Pertussis toxin, a bacterial toxin, is produced specifically by bacteria belonging to the genus Bordetella, microorganisms causative of pertussis, a disease specific to humans.

It is a well-known fact that pertussis toxin exhibits various biological actions; for example, it acts as a histamine-sensitizing factor (HSF), a leukocytosis(lymphocytosis)-promoting factor (LPF), a hemagglutinin (HA), a mouse protective antigen (MPA) and an islet-activating protein (IAP). Recent biological and protein-chemical researches have shed light on the nature of the above-mentioned factors; LPF has been found to be identical with IAP [Pittman, M.; Review of Infectious Disease,. 1, 401–412 (1979)].

The above-mentioned islet-activating protein (hereinafter also referred to as IAP) has a pharmacologial activity such that promotes insulin secretion in mammals while maintaining normal blood glucose levels for a long period; it is thought useful as a therapeutic and preventive drug for diabetes mellitus. As a result of investigation, its production method and physico-chemical properties are already known [Yajima, M.; Journal of Biochemistry, 83, 295–303 (1978)].

On the other hand, IAP has side effects such as leukocytosis promotion, histamine sensitization and hemagglutination; as a heteroprotein, it also has immunogenicity, it being of microbial derivation. It is therefore desired that a substance having islet-activating activity alone with slight or no side effects will be developed.

For the above-mentioned purpose, attempts have been made to chemically modify IAP [Nogimori, K. et al.; Biochemische Biophysische Acta, 801, 220–231 (1984) and 801, 232–243 (1984)]; however, the attenuation of side effects, specifically the reduction of antigenicity or immunogenicity, cannot be expected.

The purpose of the present invention is to produce IAP derivatives having islet-activating activity with attenuated side effects.

The present invention provides a chemically modified protein, which comprises an islet-activating protein produced by bacteria belonging to the genus Bordetella and polyethylene glycol moiety, the polyethylene glycol moiety being bound with a primary amino group of the islet-activating protein.

Any IAP produced by the bacteria belonging to the Bordetella, whether purified or semi-purified, can be used as long as it has insulin secretion promoting activity. Examples of such IAP products are those described in the above-mentioned references on IAP production and those produced as directed in the referential example below.

Primary amino groups of protein which can be used include ε-amino groups of lysine and primary amino groups at the amino terminal of protein.

The above-mentioned binding polyethylene glycol residue can be represented by the formula $$-O(CH_2CH_2O)_lR$$

wherein R is a protective group for hydroxyl and l is an integer of about 7 to 700.

As for the chemically modified protein of the present invention, it is preferable that the above-mentioned primary amino group binds to the above-mentioned polyethylene glycol via a spacer.

Any spacer can be used, as long as it mediates the binding of the abovementioned primary amino groups to polyethylene. As examples of such spacers, mention may be made of (i) groups of the formula 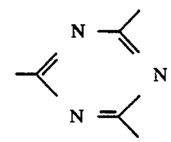 (triazines), (ii) groups of the formula $-CH_2)_m$ wherein m is an integer from 1 to 3 (alkylenes) and (iii) groups of the formula 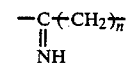 wherein n is an integer from 1 to 3 (imidates).

When the spacer is a triazine, it may have 1 or 2 polyethylene glycol molecules in each molecule, though the latter number is preferred. When the spacer is an alkylene or imidate, it is preferable that m or n is the integer 2.

It is recommended that the chemically modified protein of the present invention has IAP molecules to which 1 to 30, preferably 1 to 10 polyethylene glycol molecule(s) or spacer(s) having polyethylene glycol(s) are bound. It is also recommended that about 3 to 80%, preferably about 3 to 40%, of the primary amino groups in the IAP molecule are bound to the above-mentioned polyethylene glycols, or spacers having polyethylene glycols.

Groups which can be used for R as protective groups for hydroxyl in the above-mentioned polyethylene glycol include lower (e.g. 1 to 3 carbon atoms) alkyls and lower (e.g. 1 to 3 carbon atoms) alkanoyls. As examples of such alkyls, mention may be made of methyl, ethyl, propyl and isoproyl; and as examples of such alkanoyls, formyl, acetyl and propionyl. As the protective groups of hydroxyl, methyl is preferred. It is preferable that l is about from 80 to 300, and that the average molecular weight of the polyethylene glycol is about from 350 to 30000, preferably about 1900 to 15000.

The chemically modified protein of the present invention can be produced by reacting islet-activating protein (IAP) produced by bacteria belonging to the genus Bordetella with a polyethylene glycol-bound compound (activated PEG).

Next, the preparation of the present chemically modified protien is described.

The chemcially modified protein of the present invention wherein the spacer is a triazine can be produced by reacting IAP and a compound of the formula 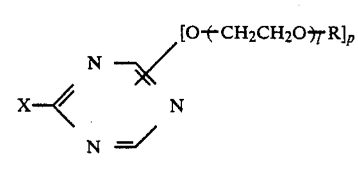 (I)

wherein R and l are as defined above, X is a halogen and p is an integer of 1 or 2. It is preferable that X is a chlorine atom.

The reaction is carried out in an aqueous solution of a buffer such as phosphate or borate at pH about 8 to 10 and at about 0° C. to room temperature for about 1 to 24 hours. Compound (I) is used in a molar ratio of 1~500 to 1 of IAP, preferably 5~200 to 1 of IAP.

The chemically modified protein of the present invention wherein the spacer is an alkylene can be produced by reacting IAP with a compound of the formula

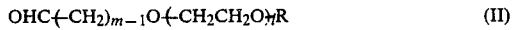

$$\text{OHC}(\text{CH}_2)_{m-1}\text{O}(\text{CH}_2\text{CH}_2\text{O})_l\text{R} \qquad (II)$$

wherein R, m and l are as defined above, in the presence of a reducing agent.

The reaction is carried out in an aqueous solution of a buffer such as phosphate or borate at pH about 6.0 to 9.0 and at about 0° C. to 50° C. for about 10 to 80 hours. Reducing agents which work well for the reaction include boronic reducing agents such as sodium borohydride and sodium cyanoborohydride. Compound (II) is used in a molar ratio of 1~1000 to 1 of IAP, preferably 5~200 to 1 of IAP; the reducer is used in a molar ratio of 1~100 to 1 of IAP.

The chemically modified protein of the present invention wherein the spacer is an imidate can be produced by reacting IAP with a compound of the formula

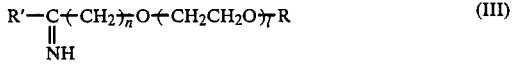

$$\text{R}'-\underset{\underset{\text{NH}}{\|}}{\text{C}}(\text{CH}_2)_n\text{O}(\text{CH}_2\text{CH}_2\text{O})_l\text{R} \qquad (III)$$

wherein R, n and l are of the same meanings as defined above, and R' is a lower alkoxy. It is preferable that alkoxys having from 1 to 3 carbon atoms (e.g. methoxy, ethoxy and propoxy) are used for R'. The above-mentioned Compound (III) can also be used in the form of a salt such as hydrochloride, sulfate or acetate.

The reaction is carried out in an aqueous solution of a buffer such as phosphate or borate under weakly alkaline conditions at pH about 7.0 to 9.0 and at about 0° C. to 40° C. for about 3 to 30 hours.

Amino group modification ratio can be varied ad libitum according to the amount of the above-mentioned activated PEG used.

Said amount to 1 mole of IAP is preferably about 5 to 1000 moles, more preferably about 50 to 500 moles in the case of which the spacer is a triazine, and preferably about 10 to 2000 moles, more preferably about 50 to 1000 mole in the case of which the spacer is an imidate or an alkylene.

If necessary, the desired chemically modified protein can be purified from the reaction liquid by using an ordinary method of protein purification such as dialysis, salting-out, ultrafiltration, ion exchange chromatography, gel filtration, high performance liquid chromatography and electrophoresis. Ultrafiltration and gel filtration are particularly efficient for the elimination of non-reacted PEG. The degree of amino group modification can be calculated by e.g. amino acid analysis following acid decomposition.

Compounds (I) and (II), starting materials, are both publicized substances; their production method and physico-chemical characteristics are described respectively, e.g., in Chemistry Letters, 773 (1980) and European patent publication No. 154316.

Compounds (III) can be produced by hydrolyzing the known compound of the formula

$$\text{NC}(\text{CH}_2)_n\text{O}-\text{CH}_2\text{CH}_2\text{O})_l\text{R} \qquad (IV)$$

wherein R, n and l are of the same meanings as defined above in the presence of a lower alkanol (methanol, ethanol, propanol etc.) and an acid (hydrogen chloride, hydrochloric acid, sulfuric acid, acetic acid etc.) in accordance with the routine procedure.

The chemically modified protein of the present invention has a strong islet-activating activity with notably attenuated leukocytosis promoting, histamine-sensitizing and hemagglutinating action, which are side effects of non-modified IAP.

In addition, the protein is notably lower in antigenicity and immunogenicity than any known non-modified IAP or relatives thereof. It is also low in toxicity.

The chemically modified protein of the present invention therefore functions very well as a preventive and therapeutic drug for diabetes mellitus in mammals (rats, mice, dogs, cats, humans etc.).

For example, when used as a therapeutic drug for diabetes mellitus, the chemically modified protein of the present invention is administered to adults in the form of injection at a dose of from 10 ng/kg to 500 μg/kg daily or in the form of oral drug in a dose of 1 mg/kg to 500 mg/kg daily, calculated on the protein basis.

Figure 2:
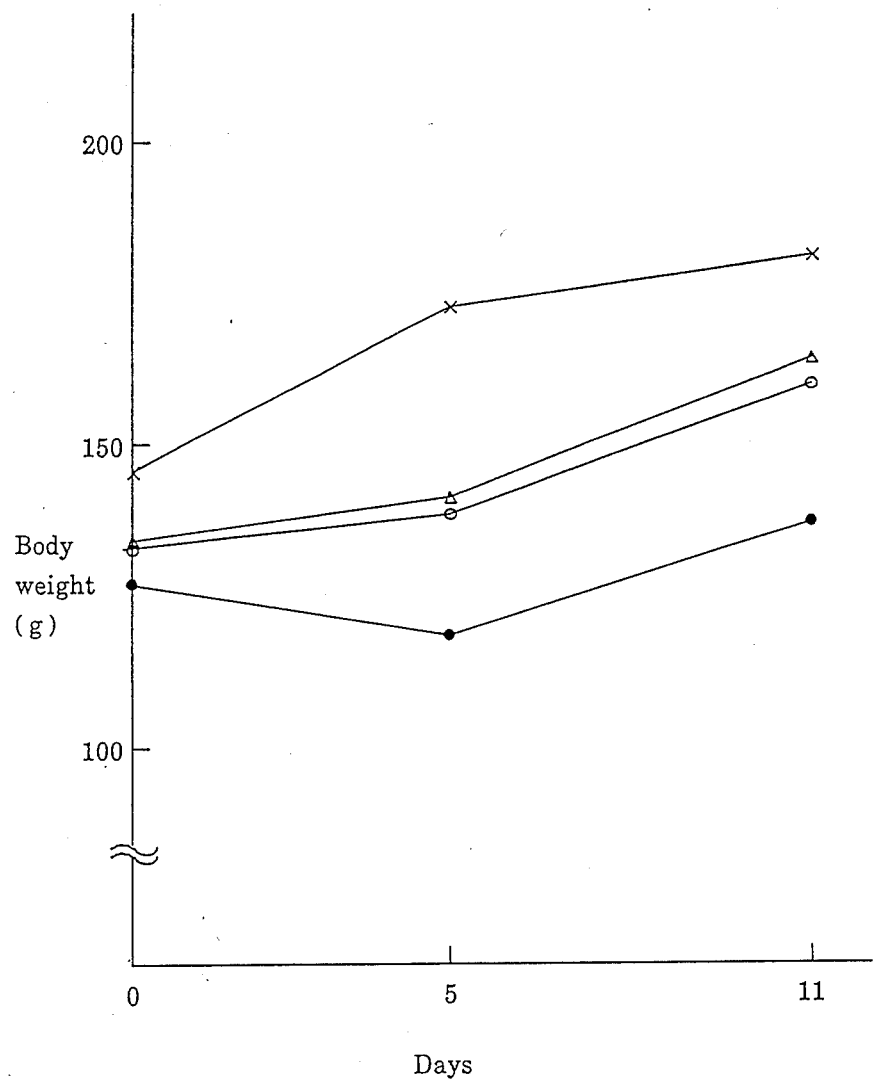
Figure 3:
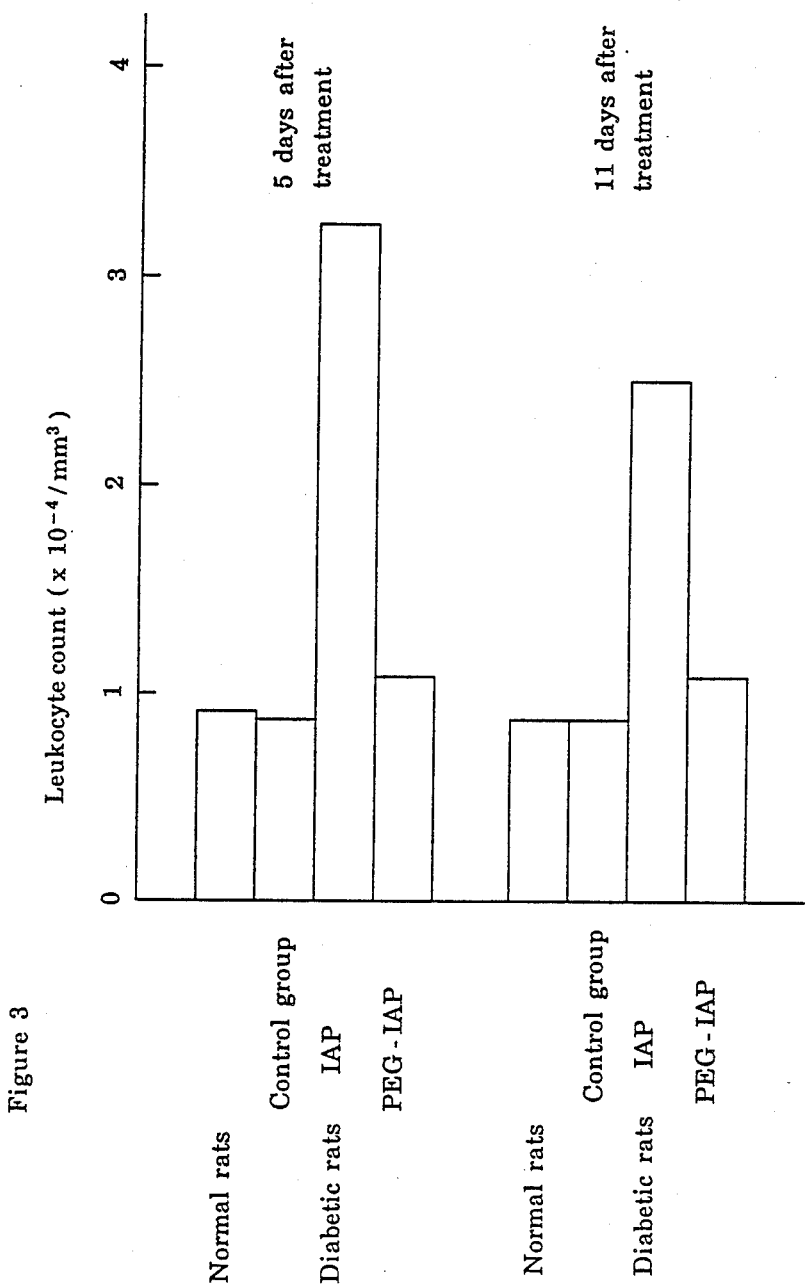

FIGS. 1, 2 and 3 respectively show the time-based changes in glucose tolerance (plasma glucose value), body weight and leukocyte count in diabetes mellitus model rats, described in Experimental Example 7. In FIGS. 1 and 2, -○-,-X-,-●- and -△- respectively indicate control group, normal rat group, IAP group and PEG-IAP group.

Action

The action of the chemically modified protein of the present invention is also shown in the experiments below.

EXPERIMENT 1

Islet Activating Activity

Non-modified IAP and the PEG-IAP obtained in Examples 1 to 4 were each dissolved in a physiological salt solution. One ml (4 μg, calculated on the protein basis) of each resulting solution was injected to SD rat (5 males in each group) via a tail vein, 3 days after which time-based changes in blood glucose level and blood insulin level were measured following an injection of a glucose solution. The animals were fasted for 24 hours before the experiment. After collecting 0.1 ml of blood via a tail vein, immediately a 20% glucose solution in a dose of 1 ml per 100 g body weight was intraperitoneally administered to each rat. 15, 30 and 60 minutes later, 0.1 ml of blood was collected from each rat. The determination of blood glucose levels was by the glucose oxidase method; that of blood insulin levels, by the double antibody technique. As shown in Tables 1 to 3, blood glucose decreased and blood insulin increased due to the administration of IAP or PEG-IAP; i.e., the PEG-modified IAP was also found to have islet-activating activity.

TABLE 1

Time-based changes in Blood Glucose Levels and Blood Insulin Levels in Rats Following Glucose Loading due to PEG-IAP obtained in Example 1

| | | Molecular Weight of PEG | Time after Glucose Administration (min.) | | | |
|---|---|---|---|---|---|---|
| | | | 0 | 15 | 30 | 60 |
| Blood glucose level (mg/dl) | Control | — | 72.0 ± 5.0 | 196.0 ± 13.7 | 169.4 ± 13.8 | 110.0 ± 11.1 |
| | Non-modified IAP | — | 69.8 ± 5.7 | 176.3 ± 31.6 | *115.8 ± 14.6 | 108.0 ± 13.6 |
| | PEG-IAP | 5000 | 67.5 ± 5.1 | 189.5 ± 18.8 | *118.8 ± 20.9 | 114.3 ± 7.8 |
| | PEG-IAP | 1900 | 69.8 ± 6.5 | *169.0 ± 33.5 | 147.2 ± 36.9 | 97.0 ± 10.9 |
| | PEG-IAP | 750 | 65.3 ± 4.9 | 165.5 ± 16.8 | 145.0 ± 26.2 | 103.3 ± 4.8 |
| | PEG-IAP | 350 | *62.8 ± 4.3 | 185.5 ± 26.2 | 157.0 ± 18.5 | 102.0 ± 8.0 |
| Blood insulin level ($\mu$U/ml) | Control | — | 1.5 ± 3.2 | 38.2 ± 47.3 | 42.1 ± 29.7 | 21.2 ± 10.1 |
| | Non-modified IAP | — | 1.5 ± 1.9 | *136.3 ± 75.0 | **308.2 ± 104.0 | *160.0 ± 127.1 |
| | PEG-IAP | 5000 | 1.8 ± 3.2 | 188.0 ± 141.4 | *164.3 ± 98.9 | 74.7 ± 98.0 |
| | PEG-IAP | 1900 | 3.8 ± 3.7 | *177.2 ± 81.6 | *144.6 ± 6.6 | 38.8 ± 12.6 |
| | PEG-IAP | 750 | 3.7 ± 2.3 | 170.7 ± 109.7 | 69.5 ± 52.4 | 27.7 ± 13.8 |
| | PEG-IAP | 350 | 5.5 ± 3.9 | *201.0 ± 122.3 | **265.4 ± 113.7 | 8.3 ± 9.1 |

Mean value ± Standard deviation *: $P < 0.05$, **: $P < 0.01$

TABLE 2

Time-based Changes in Blood Glucose Levels and Blood Insulin Levels in Rats Following Glucose Loading due to PEG-IAP obtained in Example 2

| | | Molar Ratio[1] | Time after Glucose Administration (min) | | | |
|---|---|---|---|---|---|---|
| | | | 0 | 15 | 30 | 60 |
| Blood glucose level (mg/dl) | Control | | 68.6 ± 10.0 | 177.0 ± 36.8 | 175.8 ± 26.5 | 126.2 ± 21.4 |
| | Non-modified IAP | | 70.8 ± 5.4 | 167.6 ± 22.9 | **138.5 ± 14.6 | **92.4 ± 7.4 |
| | PEG-IAP | 10 | 75.4 ± 5.9 | 202.6 ± 29.0 | **126.6 ± 26.0 | **94.6 ± 5.3 |
| | PEG-IAP | 50 | 73.8 ± 6.1 | 211.4 ± 45.7 | 158.2 ± 30.7 | **94.2 ± 7.4 |
| | PEG-IAP | 200 | *60.8 ± 4.6 | 163.2 ± 38.6 | *142.5 ± 27.6 | **98.3 ± 9.6 |
| Blood insulin level ($\mu$U/ml) | Control | | 5.9 ± 1.8 | 29.5 ± 14.0 | 26.1 ± 10.9 | 11.8 ± 5.4 |
| | Non-modified IAP | | 23.9 ± 30.6 | **106.8 ± 23.3 | **63.6 ± 33.1 | **21.0 ± 8.4 |
| | PEG-IAP | 10 | **11.7 ± 3.2 | *69.5 ± 32.4 | 32.0 ± 13.9 | 10.4 ± 1.6 |
| | PEG-IAP | 50 | *8.3 ± 2.0 | **76.2 ± 23.4 | 34.7 ± 8.8 | 12.9 ± 3.0 |
| | PEG-IAP | 200 | 6.4 ± 2.9 | *60.6 ± 28.9 | 21.8 ± 12.5 | 13.0 ± 6.0 |

Mean value ± Standard deviation*: $P < 0.05$, **: $P < 0.01$
[1]Molar ratio PEG-IAP at the time of PEG-IAP preparation (this also pertains tables below)

TABLE 3

Time-based changes in Blood Glucose Levels and Blood Insulin Levels in Rats Following Glucose Loading due to PEG-IAP obtained in Examples 3 and 4

| | | Preparation Method | Time after Glucose Administration (min.) | | | |
|---|---|---|---|---|---|---|
| | | | 0 | 15 | 30 | 60 |
| Blood glucose level (mg/dl) | Control | — | 75.0 ± 13.3 | 220.7 ± 30.4 | 179.5 ± 27.1 | 119.0 ± 17.3 |
| | Non-modified IAP | — | 80.3 ± 12.5 | *271.5 ± 44.5 | 179.5 ± 33.5 | *95.3 ± 11.2 |
| | PEG-IAP | Example 3 | 74.5 ± 8.2 | 274.0 ± 53.2 | 168.8 ± 36.2 | *86.8 ± 17.7 |
| | PEG-IAP | Example 4 | 84.8 ± 6.9 | 226.3 ± 41.2 | *140.0 ± 23.5 | 110.3 ± 4.4 |
| Blood insulin level ($\mu$U/ml) | Control | — | 9.4 ± 3.9 | 109.5 ± 50.0 | 56.3 ± 36.4 | 20.5 ± 6.8 |
| | Non-modified IAP | — | 12.9 ± 10.9 | 358.2 ± 288.0 | **258.8 ± 44.1 | **119.7 ± 72.5 |
| | PEG-IAP | Example 3 | 35.1 ± 22.0 | **312.1 ± 90.8 | 266.5 ± 211.7 | 133.9 ± 101.3 |
| | PEG-IAP | Example 4 | 28.5 ± 27.6 | 223.3 ± 61.5 | 349.8 ± 281.2 | 140.7 ± 128.7 |

Mean value ± Standard deviation*: $P < 0.05$, **: $P < 0.01$

EXPERIMENT 2

Leukocytosis-promoting Effect ($\Delta$LPF activity)

0.4 $\mu$g (calculated on the protein basis) of either non-modified IAP or the PEG-IAP obtained in Example 2 was administered via intravenous injection to each A/J mouse (male), 5 days after which leukocytes were counted, and leukocyte increase rates were calculated by subtracting the leukocyte count in the control group from that in each administration group.

$\Delta$LPF activity = (leukocyte count in each administraton group) - (leukocyte count in control group)

As shown in Table 4, leukocytosis-promoting activity is lost or attenuated with PEG-IAP.

TABLE 4

| Leukocytosis-promoting Activity | | |
|---|---|---|
| | Molar Ratio | $\Delta$ LPF Activity ($\times 10^2$/mm$^3$) |
| Non-modified IAP | | 72 |
| PEG-IAP | 10 | 11 |
| PEG-IAP | 50 | 0 |
| PEG-IAP | 200 | 0 |

EXPERIMENT 3

Histamine-sensitizing Effect

2 $\mu$g of either non-modified IAP or the PEG-IAP obtained in Example 2 was intravenously injected to each A/J mouse (10 males in each group), 4 days after which 2.5 mg of histamine was intraperitoneally injected to each mouse, and the intensity of the histamine-sensitizing effect of each treatment was determined on the basis of the number of mice which died within 1 hour. The results are shown in Table 5. Histamine-sensitizing activity is lost with PEG-IAP.

TABLE 5

| | Histamine-sensitizing Effect | |
|---|---|---|
| | Molar Ratio | Histamine-sensitizing Effect |
| Non-modified IAP | | 10 |
| PEG-IAP | 10 | 0 |
| PEG-IAP | 50 | 0 |
| PEG-IAP | 200 | 0 |

EXPERIMENT 4

Hemagglutinating Effect

Non-modified IAP and the PEG-IAP obtained in Example 2 were each serially diluted with 10 mM phosphate buffer solution (pH 7) containing 0.15M sodium chloride; 50 μl of each resulting dilution was transferred to a multi-well plate with a U-shaped base and mixed with 50 μl of 0.6% suspension of goose erythrocyte (Nihon Seibutsu Zairyo Center) in the same buffer solution. After being kept standing at room temperature for 2 hours, each mixture was visually checked for hemagglutination. As shown in Table 6, PEG-IAP has an attenuated hemagglutinating effect.

TABLE 6

| | Hemagglutinating Effect | | | | | | | |
|---|---|---|---|---|---|---|---|---|
| | Protein Concentration (μg/ml) | | | | | | | |
| | Molar Ratio | 25 | 12.5 | 6.3 | 3.1 | 1.6 | 0.78 | 0.39 | 0.20 |
| Non-modified IAP | | + | + | + | + | + | + | − | − |
| PEG-IAP | 50 | + | + | + | − | − | − | − | − |

Hemagglutination; +: Noted, −: Not noted

EXPERIMENT 5

Antigenicity

Antigenicity was determined by the enzyme immunoassay (sandwich technique). The antibody to IAP used in the experiment was anti-IAP-IgG obtained from immunized goats by affinity purification. The alkaline phosphatase-labeled anti-IAP-IgG used in the experiment was prepared by binding alkaline phosphatase (Miles, Inc. U.S.A.) to the above-mentioned anti-IAP-IgG by the glutaraldehyde method. The enzyme immunoassay procedure used in the experiment is described in detail below.

100 μl of a solution of anti-IAP-IgG (0.1 μg/ml) in 50 mM carbonate buffer solution (pH 9.7) was transferred to a 96-well microplate (Nunc, Inc. Denmark) and kept standing at 4° C. overnight for antibody adsorption. The plate was then washed with 10mM phosphate buffer solution (pH 7.4) containing 0.14M sodium chloride, 3 mM potassium chloride and 0.05% Tween 20. After adding 100 μl of a dilution of either non-IAP or the PEG-IAP in the same buffer solution, obtained in Example 1 to 4 (0 to 200 ng/ml), the plate was kept standing at room temperature for 2 hours. After washing each plate with the same buffer solution, 100 μl of alkaline phosphatase-labeled anti-IAP-IgG(about 0.25 μg/ml) in the same buffer was added, after which the plate was kept standing at room temperature for 2 hours. The plate was then washed with the same buffer solution and assayed for alkaline phosphatase activity. Alkaline phosphatase activity was determined by measuring the absorbance at a wavelength of 405 nm, the samples having previously reacted at room temperature for 1 hour with 200 μl of a solution of p-nitrophenylphosphate (1 mg/ml) in a 1M diethanolamine buffer soltuion (pH 9.8) containing 0.01% magnesium chloride hexahydrate, using a Corona MTP-12 microplate photometer. The results are shown in Table 7. Antigenicity levels are shown in % absorbance ratio, calculated on the basis of the absorbance of non-modified IAP, which was taken as 100%.

TABLE 7

| | | Antigenicity | | |
|---|---|---|---|---|
| | Preparation method | Molecular weight of PEG | Modification Ratio (%) | Antigenicity Level (%) |
| Non-modified IAP | — | — | — | 100 |
| PEG-IAP | Example 1 | 350 | 22.5 | 76 |
| PEG-IAP | Example 1 | 750 | 30.5 | 59 |
| PEG-IAP | Example 1 | 1900 | 15.8 | 60 |
| PEG-IAP | Example 1 | 5000 | 16.7 | 40 |
| PEG-IAP | Example 2 | 5000 | 3.0 | 60 |
| PEG-IAP | Example 2 | 5000 | 19.7 | 38 |
| PEG-IAP | Example 2 | 5000 | 35.8 | 10 |
| PEG-IAP | Example 3 | 5000 | 37.0 | 78 |
| PEG-IAP | Example 4 | 5000 | 16.4 | 88 |

EXPERIMENT 6

Immunogenicity

This experiment was conducted in accordance with the method described in the Journal of Immunological Methods, 14, 381 (1977). After emulsification with Freund's complete adjuvant (FCA), non-modified IAP or the PEG-IAP obtained in Example 2 (2 μg, calculated on the protein basis) was intraperitoneally administered to each A/J mouse (8 animals in each group), 14 and 28 days after which additional administraton was carried out. Starting on the 14th day following the first administration, blood samples were obtained from the retro orbital plexus of each mouse at 7-day intervals; serum anti-body production was evaluated by the passive cutaneous anaphylactic (PCA) reaction using rats. Each serum sample (0.1 ml), previously diluted, was intracutaneously injected to each rat, 4 hours after which each rat was intravenously injected 2 ml of a mixture of 100 μg non-modified IAP and 20 mg Evans blue, to determine the vascular permeability of the dye, which was used as evaluation criterion for PCA titers. The results are shown in Table 8, where the values are shown in maximum dilution rates of serum samples positive for PCA reaction. Anti-IAP antibody production was noted in the case of non-modified IAP, PEG-IAP 10 and PEG-IAP 50, while not noted in the case of PEG-IAP 200.

TABLE 8

| | Immunogenicity | | | | |
|---|---|---|---|---|---|
| | | Date of PCA-Titer Evaluation | | | |
| | Molar ratio | 14 | 21 | 28 | 35 |
| Non-modified IAP | | —* | — | — | 16 |
| PEG-IAP | 10 | — | — | 4 | 32 |
| PEG-IAP | 50 | — | — | — | 16 |
| PEG-IAP | 200 | — | — | — | — |

*<4

EXPERIMENT 7

Improvement of Glucose Tolerance in Diabetes Mellitus Model Rats

After subcutaneous injection of 120 mg/kg streptozotocin at the age of 1.5 day, female Wistar-Kyoto rats were raised until the 8th week of age to obtain diabetes mellitus model rats. Each model rat received via intravenously injected 2 μg of either non-modified IAP or the PEG-IAP obtained in Example 2, 6 days after which the glucose tolerance of each rat was determined. In addition, body weight and leukocyte count were measured 5 day and 11 days after injection. Glucose tolerance was determined as follows: 0.1 ml of blood was collected via a tail vein (each rat being fasted for 24 hours before the initiation of the experiment), immediately after which glucose (2 g/kg) was orally administered to each rat. 15, 30, 60 and 120 minutes later, 0.1 ml of blood was collected from each rat. Plasma glucose contents of blood samples were determined by the glucose oxidase method. FIGS. 1, 2 and 3 respectively show the plasma glucose contents, body weights and leukocyte counts.

As shown in FIG. 1, diabetic rats showed a considerably worsened glucose tolerance in comparison to normal rats. In the groups administered non-modified IAP or PEG-IAP, however, glucose tolerance was improved to a level comparable with that in normal rats. In addition, in the group administered non-modified IAP, body weight decreased and leukocyte count increased to a level 3 times that in the control group. On the other hand, the group administered PEG-IAP was hardly different from control group, in either body weight or leukocyte count.

Judging from these results, it is obvious that while maintaining a glucose tolerance improving effect nearly equivalent to that of non-modified IAP, some side effects of IAP, i.e. body weight-reducing effect and leukocytosis-promoting effect, are lost when IAP is modified with PEG.

The present invention is more concretely described by the following Reference Examples and Working Examples.

REFERENCE EXAMPLE 1

Preparation of IAP

A high avian hemagglutination value (HA value) fraction containing a small amount of endotoxin, produced in accordance with the method described in Example 1 of European Patent Publication No. 47802, previously heated at 100° C. for 3 minutes, was passed through a hydroxyapatite column equilibrated to pH 8.0 to remove FHA. The fraction not adsorbed to the column was adjusted to pH 6.0 with hydrochloric acid and passed through another hydroxyapatite column equilibrated to pH 6.0. Adsorbed crude IAP was eluated with a 0.1M phosphate buffer solution (pH 7.0) containing 0.5M sodium chloride, then passed through a column packed with anti-FHA-bound Sepharose, after which it was purified by sucrose density gradient centrifugation to obtain purified IAP, which was used in Examples.

REFERENCE EXAMPLE 2

Preparation of 2,4-bis(O-polyethylene glycol methyl ether)-6-chloro-S-triazine To the mixture containing 40 g of polyethylene glycol methyl ether (average molecular weight: 5000), 200 ml of benzene, 20 g of anhydrous sodium carbonate and 10 g of molecular sieve 3A (Wako Pure Chemicals, Japan) was added 730 mg of cyanuric chloride. The resulting mixture was heated at 80° C. with stirring for 20 hours. Then 400 ml of petroleum ether was added to the heated mixture to precipitate 2.4-bis(O-polyethylene glycol methyl ether)-6-chloro-S-triazine.

The obtained precipitate was dissolved in benzene to remove nonreacted cyanuric chloride. After this procedure being repeated three times, the precipitate was dried in a desiccator under reduced pressure to obtain 36 g of 2,4-bis(O-polyethylene glycol methyl ether)-6-chloro-S-triazine.

The chlorine content of 2,4-bis(O-polyethylene glycol methyl ether)-6-chloro-S-triazine measured by the Maricle's method [Analytical Chemistry, 35, 683 (1963)] was 0.32%, which was in accord with 0.35%, its theoretical value.

Each polyethylene glycol methyl ether (average molecular weight: 350, 750 or 1900) was treated in the same manner as described above to obtain its corresponding 2,4-bis(O-polyethylene glycol methyl ether)-6-chloro-S-triazine.

The yields were 10.0 g, 13.2 g and 33.6 g, respectively.

The chlorine contents of the obtained 2,4-bis(O-polyethylene glycol methyl ether)-6-chloro-S-triazine were 7.5%, 4.2% and 1.5%, respectively, which were substantially in accord with 7.6%, 4.1% and 1.7%, their theoretical values, respectively.

The 2,4-bis(O-polyethylene glycol methyl ether)-6-chloro-S-triazine having an average molecular weight 350 or 750 was like syrup at ordinary temperature.

REFERENCE EXAMPLE 3

Preparation of polyethylene glycol mono-methyl ether aldehyde

Polyethylene glycol methyl ether (5 g, average molecular weight: 5000) was dissolved in 100 ml of methylene chloride. To the solution was added 330 mg of pyridinium chloro-chromate and then stirred at room temperature for 12 hours.

The obtained reaction solution was diluted with two times volume of methylene chloride and then poured into a florisil column (Serva, West Germany, column size: 6×10 cm), washed with methylene chloride then chloroform, and then eluated with methanol-chloroform (1:9). After collecting positive fractions in a 2,4-dinitrophenyl hydrazine test, the solvent was evaporated under reduced pressure to obtain the objective compound as a crystalline wax. Yield: 1.5 g (30%), Thin layer chromatography:Rf=0.08 (solvent system; chloroform:methanol:acetic acid=9:1:0.5, carrier; silica gel), The absorption of an aldehyde group was recognized at 96.2 PPM in the hydrating form (—$\underline{C}H(OH)_2$) in 13C-NMR.

REFERENCE EXAMPLE 4

Preparation of polyethylene glycol imide ester

Two grams of polyethylene glycol methyl ether mono-β-cyanoethyl ether prepared from polyethylene glycol methyl ether (average molecular weight:5000) was dissolved in 15 ml of anhydrous methanol. To the solution was blown dried hydrogen chloride under −20° C. to saturate it. After being plugged up, it was allowed to stand in a refrigerator for 3 days. To this was added anhydrous ether and allowed to stand in a refrigerator again. After 4 hours, the upper ether layer was decanted. To the resulting layer was added anhydrous ether, vigorously stirred and standed in a refrigerator for an hour to obtain a solid. The solid was well washed with anhydrous ether after pouring out ether, standed in a refrigerator till a solid precipitated and then the resulting ether layer was poured out. The solid was well washed by repeating this procedure twice. The obtained solid was sucked dry in a desiccator containing phosphorus pentoxide and solid NaOH for an hour to obtain 1.5 g of polyethylene glycol imide ester (average molecular weight: 5000).

In NMR (solvent; d$_6$-DMSO, 90 MHz), a triplet according to

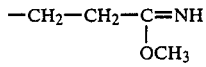

was recognized at δ2.3, in IR, the absorption according to —CN was found to disappear.

EXAMPLE 1

Preparation of PEG-IAP

To 2.5 mg of IAP was added 2,4-bis(O-polyethylene glycol methyl ether)-6-chloro-S-triazine (average molecular weight: 350, 750, 1900 or 5000) obtained in Reference Example 2 in a molar ratio of 200 to 1 of IAP. The mixture was reacted in 25 ml of 0.1 M borate buffer (pH 9.0) at 4° C. for 2 hours and then 25ml of 0.2 M phosphate buffer (pH 7) was added to stop the reaction. The reacted mixture was subjected to ultrafiltration (PM-30 membrane, Amicon, U.S.A.) to remove non-reacted PEG and 2.0 ml of the concentrate was purified by gel filtration using a column (1.8×77 cm) packed with Sephacryl S-200 (Pharmacia, Sweden) to obtain PEG-IAP. Protein contents were determined by Lowry's method. Amino group modification ratios were calculated on the basis of the amount of free amino groups as measured by the fluorescamine method [Archieves of Biochemistry and Biophisics, 155, 213–220 (1973)]. The results are shown in Table 9.

TABLE 9

| Amino Group Modification ratios of PEG-IAP | | |
|---|---|---|
| | Molecular Weight of PEG | Modification Ratio (%) |
| PEG-IAP | 350 | 22.5 |
| PEG-IAP | 750 | 30.5 |
| PEG-IAP | 1900 | 15.8 |
| PEG-IAP | 5000 | 16.7 |

EXAMPLE 2

Preparation of PEG-IAP

To 1 mg of IAP was added 2,4-bis(O-polyethylene glycol methyl ether)-6-chloro-S-triazine (average molecular weight: 5000) obtained in Reference Example 2 in a molar ratio of 10, 50 or 200 to 1 of IAP. The mixture was reacted in 4.0 ml of 0.1 M borate buffer (pH 9) at 4° C. for 2 hours and then 4.0 ml of 0.1 M phosphate buffer (pH 7.0) was added to stop the reaction.

The reacted mixture was subjected to ultrafiltration (PM-30 membrane, Amicon, U.S.A.) to remove non-reacted PEG and 2.0 ml of the concentrate was purified by gel filtration using a column (1.8×77 cm) packed with Sephacryl S-200 (Pharmacia, Sweden) to obtain PEG-IAP. Protein contents were determined by Lowry's method. Amino group modification ratios were calculated on the basis of the amount of free amino groups as measured by the fluorescamine method. The results are shown in Table 10.

TABLE 10

| Amino Group Modification Ratios of PEG-IAP | | |
|---|---|---|
| | Molar Ratio | Modification Ratio (%) |
| PEG-IAP | 10 | 3.0 |
| PEG-IAP | 50 | 19.7 |
| PEG-IAP | 200 | 35.8 |

EXAMPLE 3

Preparation of PEG-IAP

To 2 mg of IAP was added polyethylene glycol methyl ether aldehyde obtained in Reference Example 3 in a molar ratio of 1000 to 1 of IAP. The mixture was reacted in 2 ml of 0.1 M phosphate buffer (pH 7.0) containing 2 M urea at room temperature for 30 minutes. After 50 μl of pyridine borane (50 mg/ml) in methanol was added, the mixture was reacted at room temperature for 2 hours. To the reacted mixture was added 2 ml of 1 M glycine to stop the reaction. The reacted mixture was subjected to ultrafiltration (PM-30 membrane, Amicon, U.S.A.) to remove non-reacted PEG and 2.0 ml of the concentrate was purified by gel filtration using a column (1.8×77 cm) packed with Sephacryl S-200 (Pharmacia, Sweden) to obtain PEG-IAP.

The amino group modification ratio measured by the fluorescamine method was 37.0%.

EXAMPLE 4

Preparation of PEG-IAP

To 2 mg of IAP was added polyethylene glycol imide ester obtained in Reference Example 4 in a molar ration of 2000 to 1 of IAP. The mixture was reacted in 2 ml of 0.1 M phosphate buffer (pH 7.0) containing 2M urea at 4° C. for 2 hours. To the reacted mixture was added 40 ml of 1M ammonium acetate (pH 6.0) to stop the reaction. The reacted mixture was subjected to ultrafiltration (PM-30 membrane, Amicon, USA) to remove non-reacted PEG and 2.0 ml of the concentrate was purified by gel filtration using a column (1.8×77 cm) packed with Sephacryl S-200 (Pharmacia, Sweden) to obtain PEG-IAP. The amino group modification ratio measured by the fluorescamine method was 16.4%.

What is claimed is:

1. A chemically modified protein with insulin secreting activity which comprises an islet-activating protein produced by bacteria belonging to the genus Bordetella and polyethylene glycol moiety of the formula

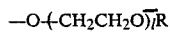

where R is a protective group for hydroxyl and l is an integer of about 7 to 700, the polyethylene glycol moiety being bound with a primary amino group of the islet-activating protein.

2. A chemically modified protein as claimed in claim 1, wherein the islet-activating protein is bound with the polyethylene glycol via a spacer.

3. A chemically modified protein as claimed in claim 2, wherein the spacer is a group of the formula

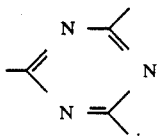

4. A chemically modified protein as claimed in claim 2, wherein the spacer is a group of the formula

wherein m is an integer from 1 to 3.

5. A chemically modified protein as claimed in claim 4, wherein m is 2.

6. A chemically modified protein as claimed in claim 2, wherein the spacer is a group of the formula

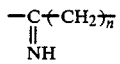

wherein n is an integer from 1 to 3.

7. A chemically modified protein as claimed in claim 6, wherein n is 2.

8. A chemically modified protein as claimed in claim 2, wherein the average molecular weight of the polyethylene glycol is 350 to 30000.

9. A chemically modified protein as claimed in claim 2, wherein the average molecular weight of the polyethylene glycol is 1900 to 15000.

10. A chemically modified protein as claimed in claim 2, wherein the average molecular weight of the polyethylene glycol is 5000.

11. A chemically modified protein as claimed in claim 2, wherein the islet-activating protein is bound with 1 to 30 spacers.

12. A chemically modified protein as claimed in claim 2, wherein the islet-activating protein is bound with 1 to 10 spacers.

13. A chemically modified protein as claimed in claim 2, wherein the modification ratio of the primary amino group is 3 to 80%.

14. A chemically modified protein as claimed in claim 2, wherein the modification ratio of the primary amino group is 3 to 40%.

15. A chemically modified protein as claimed in claim 2, wherein R is $C_{1-3}$ alkyl or $C_{1-3}$ alkanoyl.

16. A chemically modified protein as claimed in claim 2, wherein R is methyl.

* * * * *